US008173776B1

(12) United States Patent
De Boer et al.

(10) Patent No.: US 8,173,776 B1
(45) Date of Patent: *May 8, 2012

(54) RECOMBINANT GELATINS

(75) Inventors: Arjo Lysander De Boer, Tilburg (NL); Hendrik Van Urk, Tilburg (NL); Jan Bastiaan Bouwstra, Tilburg (NL); Peter Franciscus Theresius Maria Van Asten, Tilburg (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,833

(22) Filed: Dec. 2, 2011

Related U.S. Application Data

(62) Division of application No. 12/527,900, filed as application No. PCT/NL2008/050098 on Feb. 21, 2008.

(30) Foreign Application Priority Data

| Feb. 21, 2007 | (EP) | 07102838 |
| Feb. 21, 2007 | (EP) | 07102839 |
| Sep. 12, 2007 | (EP) | 07116189 |
| Sep. 12, 2007 | (EP) | 07116193 |
| Jan. 16, 2008 | (EP) | 08100556 |

(51) Int. Cl.
*A61K 38/17* (2006.01)
*A23J 1/00* (2006.01)
*C07H 21/02* (2006.01)
*C12P 1/00* (2006.01)

(52) U.S. Cl. ......... 530/356; 530/412; 435/41; 536/23.1

(58) Field of Classification Search ............ None
See application file for complete search history.

(56) References Cited

U.S. PATENT DOCUMENTS

| 4,855,134 | A | 8/1989 | Yamahira et al. | 424/85.7 |
| 5,002,769 | A | 3/1991 | Friedman | 424/422 |
| 5,023,082 | A | 6/1991 | Friedman et al. | 424/426 |
| 5,399,361 | A | 3/1995 | Song et al. | 424/486 |
| 5,512,301 | A | 4/1996 | Song et al. | 424/484 |
| 5,597,578 | A | 1/1997 | Brown et al. | 424/422 |
| 5,733,994 | A | 3/1998 | Koepff et al. | 527/207 |
| 5,897,879 | A | 4/1999 | Friedman et al. | 424/486 |
| 6,068,854 | A | 5/2000 | Wunderlich et al. | 424/464 |
| 6,140,072 | A | 10/2000 | Ferrari et al. | 435/69.1 |
| 6,150,081 | A | 11/2000 | Van Heerde et al. | 430/569 |
| 6,342,250 | B1 | 1/2002 | Masters | 424/484 |
| 6,458,386 | B1 | 10/2002 | Schacht et al. | 424/488 |
| 6,831,058 | B1 | 12/2004 | Ikada et al. | 514/2 |
| 6,992,172 | B1 | 1/2006 | Chang et al. | 530/354 |
| 7,517,954 | B2 | 4/2009 | Bouwstra et al. | 530/350 |
| 2002/0028243 | A1 | 3/2002 | Masters | 424/484 |
| 2002/0106410 | A1 | 8/2002 | Masters | 424/484 |
| 2003/0007991 | A1 | 1/2003 | Masters | 424/423 |
| 2003/0064074 | A1 | 4/2003 | Chang et al. | 424/184.1 |
| 2004/0237663 | A1 | 12/2004 | Farber et al. | 73/861.08 |
| 2005/0058703 | A1 | 3/2005 | Chang et al. | 424/456 |
| 2005/0119170 | A1 | 6/2005 | Bouwstra et al. | 514/12 |
| 2005/0147690 | A1 | 7/2005 | Masters et al. | 424/499 |
| 2005/0208141 | A1 | 9/2005 | Farber et al. | 424/488 |
| 2005/0229264 | A1 | 10/2005 | Chang et al. | 800/8 |
| 2005/0238663 | A1 | 10/2005 | Hunt | 424/239.1 |
| 2006/0024346 | A1 | 2/2006 | Brody et al. | 424/423 |
| 2006/0024361 | A1 | 2/2006 | Odidi et al. | 424/464 |
| 2006/0068013 | A1 | 3/2006 | DiTizio et al. | 424/484 |
| 2006/0121609 | A1 | 6/2006 | Yannas et al. | 435/395 |
| 2006/0147501 | A1 | 7/2006 | Hillas et al. | 424/443 |
| 2006/0177492 | A1 | 8/2006 | Yunoki et al. | 424/445 |
| 2006/0204511 | A1 | 9/2006 | Bouwstra et al. | 424/185.1 |
| 2006/0241032 | A1 | 10/2006 | Bouwstra et al. | 514/12 |
| 2006/0251719 | A1 | 11/2006 | Tabata | 424/468 |
| 2007/0004034 | A1 | 1/2007 | Bouwstra et al. | 435/289.1 |
| 2007/0009580 | A1 | 1/2007 | DiCosmo et al. | 424/443 |
| 2007/0031501 | A1 | 2/2007 | Van Es et al. | 424/488 |
| 2007/0190153 | A1 | 8/2007 | Farber | 424/488 |
| 2007/0196496 | A1 | 8/2007 | Farber et al. | 424/488 |
| 2008/0107666 | A1 | 5/2008 | van Es et al. | 424/185.1 |
| 2008/0113910 | A1 | 5/2008 | Bouwstra et al. | 514/12 |
| 2008/0114078 | A1 | 5/2008 | Bouwstra et al. | 514/774 |
| 2008/0167446 | A1 | 7/2008 | Bouwstra et al. | 530/354 |
| 2008/0274957 | A1 | 11/2008 | Bouwstra et al. | 514/12 |
| 2009/0143568 | A1 | 6/2009 | Chang et al. | 530/354 |

FOREIGN PATENT DOCUMENTS

| JP | 2005-211477 | 8/2005 |
| WO | WO 2004/056976 | 7/2004 |
| WO | WO 2004/085473 | 10/2004 |
| WO | WO 2005/011739 | 2/2005 |
| WO | WO 2007/073190 | 6/2007 |

OTHER PUBLICATIONS

Werten et al., "High-yield Secretion of Recombinant Gelatins by *Pichia pastoris*", Yeast, 15:1087-1096 (1999).

Báez at al., "Recombinant microbial systems for the production of human collagen and gelatin", Appl. Microbiol Biotechnol., 69:245-252 (2005).

Werten et al., "Secreted production of a custom-designed, highly hydrophilic gelatin in *Pichia pastoris*", Protein Engineering, 14(6):447-454 (2001). Olsen et al., "Recombinant collagen and gelatin for drug delivery", Advanced Drug Delivery Reviews, Amsterdam, NL, 55(12):1547-1567 (2003).

Sutter at al., "Recombinant gelatin hydrogels for the sustained release of proteins", Journal of Controlled Release, 119:301-312 (2007).

Extracts from gmap-gelatin.com, dated Aug. 25, 2006.

*Primary Examiner* — Suzanne M Noakes

(74) *Attorney, Agent, or Firm* — Morgan, Lewis & Bockius LLP

(57) ABSTRACT

The invention concerns a recombinant CBE gelatin and recombinant gelatins having multimers of the CBE monomer sequence that are of particular use in several applications involving cell attachment such as in cell culture work and applications involving cell cultures of anchor dependent cells and also in a variety of medical applications.

22 Claims, No Drawings

SEQUENCE LISTING

<160> NUMBER OF SEQ ID NOS: 11

<210> SEQ ID NO 1
<211> LENGTH: 189
<212> TYPE: PRT
<213> ORGANISM: Artificial
<220> FEATURE:
<223> OTHER INFORMATION: CBE monomer

<400> SEQUENCE: 1

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro
            180                 185

<210> SEQ ID NO 2
<211> LENGTH: 378
<212> TYPE: PRT
<213> ORGANISM: Artificial
<220> FEATURE:
<223> OTHER INFORMATION: CBE2

<400> SEQUENCE: 2

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

-continued

Pro Lys Gly Ala Asp Gly Ala Pro Lys Asp Gly Val Arg Gly Leu
            115                 120                 125

Ala Gly Pro Ile Gly Pro Pro Gly Pro Ala Gly Ala Pro Gly Ala Pro
        130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Ala Gly Pro
    210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
        275                 280                 285

Gly Leu Pro Gly Pro Lys Gly Glu Arg Gly Asp Ala Gly Pro Lys Gly
    290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
        355                 360                 365

Asp Gly Val Arg Gly Leu Ala Gly Pro Pro
    370                 375

<210> SEQ ID NO 3
<211> LENGTH: 567
<212> TYPE: PRT
<213> ORGANISM: Artificial
<220> FEATURE:
<223> OTHER INFORMATION: CBE3

<400> SEQUENCE: 3

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

```
Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
            165                 170                 175

Pro Gly Lys Asp Gly Val Arg Gly Leu Ala Gly Pro Gly Ala Pro
        180                 185                 190

Gly Leu Gln Gly Ala Pro Gly Leu Gln Gly Met Pro Gly Glu Arg Gly
    195                 200                 205

Ala Ala Gly Leu Pro Gly Pro Lys Gly Glu Arg Gly Asp Ala Gly Pro
    210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
            245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
        275                 280                 285

Gly Leu Pro Gly Pro Lys Gly Glu Arg Gly Asp Ala Gly Pro Lys Gly
    290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
            325                 330                 335

Gly Met Pro Gly Glu Arg Gly Ala Ala Gly Leu Pro Gly Pro Lys Gly
        340                 345                 350

Glu Arg Gly Asp Ala Gly Pro Lys Gly Ala Asp Gly Ala Pro Gly Lys
    355                 360                 365

Asp Gly Val Arg Gly Leu Ala Gly Pro Pro Gly Ala Pro Gly Leu Gln
    370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
            405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
        435                 440                 445

Pro Lys Gly Ala Asp Gly Ala Pro Gly Lys Asp Gly Val Arg Gly Leu
    450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
            485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
        515                 520                 525
```

```
Gly Glu Arg Gly Ala Ala Gly Leu Pro Gly Pro Lys Gly Glu Arg Gly
        530                 535                 540

Asp Ala Gly Pro Lys Gly Ala Asp Gly Ala Pro Gly Lys Asp Gly Val
545                 550                 555                 560

Arg Gly Leu Ala Gly Pro Pro
                565

<210> SEQ ID NO 4
<211> LENGTH: 756
<212> TYPE: PRT
<213> ORGANISM: Artificial
<220> FEATURE:
<223> OTHER INFORMATION: CBE4

<400> SEQUENCE: 4

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
                100                 105                 110

Pro Lys Gly Ala Asp Gly Ala Pro Gly Lys Asp Gly Val Arg Gly Leu
            115                 120                 125

Ala Gly Pro Ile Gly Pro Pro Gly Pro Ala Gly Ala Pro Gly Ala Pro
        130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Ala Gly Pro
210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
        275                 280                 285

Gly Leu Pro Gly Pro Lys Gly Glu Arg Gly Asp Ala Gly Pro Lys Gly
        290                 295                 300

Ala Asp Gly Ala Pro Gly Lys Asp Gly Val Arg Gly Leu Ala Gly Pro
305                 310                 315                 320
```

-continued

```
Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
        355                 360                 365

Asp Gly Val Arg Gly Leu Ala Gly Pro Pro Gly Ala Pro Gly Leu Gln
    370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
                405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
        435                 440                 445

Pro Lys Gly Ala Asp Gly Ala Pro Gly Lys Asp Gly Val Arg Gly Leu
    450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
        515                 520                 525

Gly Glu Arg Gly Ala Ala Gly Leu Pro Gly Pro Lys Gly Glu Arg Gly
    530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
                565                 570                 575

Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
        595                 600                 605

Pro Gly Ala Pro Gly Leu Gln Gly Met Pro Gly Glu Arg Gly Ala Ala
    610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655

Ile Gly Pro Pro Gly Glu Arg Gly Ala Ala Gly Leu Pro Gly Pro Lys
            660                 665                 670

Gly Glu Arg Gly Asp Ala Gly Pro Lys Gly Ala Asp Gly Ala Pro Gly
        675                 680                 685

Lys Asp Gly Val Arg Gly Leu Ala Gly Pro Ile Gly Pro Pro Gly Pro
    690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
            740                 745                 750
```

```
Ala Gly Pro Pro
        755

<210> SEQ ID NO 5
<211> LENGTH: 945
<212> TYPE: PRT
<213> ORGANISM: Artificial
<220> FEATURE:
<223> OTHER INFORMATION: CBE5

<400> SEQUENCE: 5

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Ala Gly Pro
    210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
        275                 280                 285

Gly Leu Pro Gly Pro Lys Gly Glu Arg Gly Asp Ala Gly Pro Lys Gly
    290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350
```

-continued

Glu Arg Gly Asp Ala Gly Pro Lys Gly Ala Asp Gly Ala Pro Gly Lys
        355                 360                 365

Asp Gly Val Arg Gly Leu Ala Gly Pro Pro Gly Ala Pro Gly Leu Gln
    370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
                405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
            435                 440                 445

Pro Lys Gly Ala Asp Gly Ala Pro Gly Lys Asp Gly Val Arg Gly Leu
    450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
    530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
                565                 570                 575

Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
    595                 600                 605

Pro Gly Ala Pro Gly Leu Gln Gly Met Pro Gly Glu Arg Gly Ala Ala
    610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655

Ile Gly Pro Pro Gly Glu Arg Gly Ala Ala Gly Leu Pro Gly Pro Lys
            660                 665                 670

Gly Glu Arg Gly Asp Ala Gly Pro Lys Gly Ala Asp Gly Ala Pro Gly
            675                 680                 685

Lys Asp Gly Val Arg Gly Leu Ala Gly Pro Ile Gly Pro Pro Gly Pro
    690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
            740                 745                 750

Ala Gly Pro Pro Gly Ala Pro Gly Leu Gln Gly Ala Pro Gly Leu Gln
            755                 760                 765

Gly Met Pro Gly Glu Arg Gly Ala Ala Gly Leu Pro Gly Pro Lys Gly
    770                 775                 780

```
Glu Arg Gly Asp Ala Gly Pro Lys Ala Asp Gly Ala Pro Gly Ala
785                 790                 795                 800

Pro Gly Leu Gln Gly Met Pro Gly Glu Arg Gly Ala Ala Gly Leu Pro
                805                 810                 815

Gly Pro Lys Gly Glu Arg Gly Asp Ala Gly Pro Lys Gly Ala Asp Gly
            820                 825                 830

Ala Pro Gly Lys Asp Gly Val Arg Gly Leu Ala Gly Pro Ile Gly Pro
        835                 840                 845

Pro Gly Glu Arg Gly Ala Ala Gly Leu Pro Gly Pro Lys Gly Glu Arg
    850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
                885                 890                 895

Pro Gly Ala Pro Gly Leu Gln Gly Met Pro Gly Glu Arg Gly Ala Ala
            900                 905                 910

Gly Leu Pro Gly Pro Lys Gly Glu Arg Gly Asp Ala Gly Pro Lys Gly
        915                 920                 925

Ala Asp Gly Ala Pro Gly Lys Asp Gly Val Arg Gly Leu Ala Gly Pro
    930                 935                 940

Pro
945

<210> SEQ ID NO 6
<211> LENGTH: 1134
<212> TYPE: PRT
<213> ORGANISM: Artificial
<220> FEATURE:
<223> OTHER INFORMATION: CBE6

<400> SEQUENCE: 6

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190
```

```
Gly Leu Gln Gly Ala Pro Gly Leu Gln Gly Met Pro Gly Glu Arg Gly
            195                 200                 205

Ala Ala Gly Leu Pro Gly Pro Lys Gly Glu Arg Gly Asp Ala Gly Pro
210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
            245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
            275                 280                 285

Gly Leu Pro Gly Pro Lys Gly Glu Arg Gly Asp Ala Gly Pro Lys Gly
            290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
            355                 360                 365

Asp Gly Val Arg Gly Leu Ala Gly Pro Pro Gly Ala Pro Gly Leu Gln
            370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
                405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
            435                 440                 445

Pro Lys Gly Ala Asp Gly Ala Pro Gly Lys Asp Gly Val Arg Gly Leu
            450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
            530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
                565                 570                 575

Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
            595                 600                 605

Pro Gly Ala Pro Gly Leu Gln Gly Met Pro Gly Glu Arg Gly Ala Ala
            610                 615                 620
```

```
Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655

Ile Gly Pro Pro Gly Glu Arg Gly Ala Ala Gly Leu Pro Gly Pro Lys
            660                 665                 670

Gly Glu Arg Gly Asp Ala Gly Pro Lys Gly Ala Asp Gly Ala Pro Gly
        675                 680                 685

Lys Asp Gly Val Arg Gly Leu Ala Gly Pro Ile Gly Pro Pro Gly Pro
690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
                740                 745                 750

Ala Gly Pro Pro Gly Ala Pro Gly Leu Gln Gly Ala Pro Gly Leu Gln
                755                 760                 765

Gly Met Pro Gly Glu Arg Gly Ala Ala Gly Leu Pro Gly Pro Lys Gly
        770                 775                 780

Glu Arg Gly Asp Ala Gly Pro Lys Gly Ala Asp Gly Ala Pro Gly Ala
785                 790                 795                 800

Pro Gly Leu Gln Gly Met Pro Gly Glu Arg Gly Ala Ala Gly Leu Pro
                805                 810                 815

Gly Pro Lys Gly Glu Arg Gly Asp Ala Gly Pro Lys Gly Ala Asp Gly
                820                 825                 830

Ala Pro Gly Lys Asp Gly Val Arg Gly Leu Ala Gly Pro Ile Gly Pro
            835                 840                 845

Pro Gly Glu Arg Gly Ala Ala Gly Leu Pro Gly Pro Lys Gly Glu Arg
        850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
                885                 890                 895

Pro Gly Ala Pro Gly Leu Gln Gly Met Pro Gly Glu Arg Gly Ala Ala
            900                 905                 910

Gly Leu Pro Gly Pro Lys Gly Glu Arg Gly Asp Ala Gly Pro Lys Gly
        915                 920                 925

Ala Asp Gly Ala Pro Gly Lys Asp Gly Val Arg Gly Leu Ala Gly Pro
930                 935                 940

Pro Gly Ala Pro Gly Leu Gln Gly Ala Pro Gly Leu Gln Gly Met Pro
945                 950                 955                 960

Gly Glu Arg Gly Ala Ala Gly Leu Pro Gly Pro Lys Gly Glu Arg Gly
                965                 970                 975

Asp Ala Gly Pro Lys Gly Ala Asp Gly Ala Pro Gly Ala Pro Gly Leu
            980                 985                 990

Gln Gly Met Pro Gly Glu Arg Gly Ala Ala Gly Leu Pro Gly Pro Lys
        995                 1000                1005

Gly Glu Arg Gly Asp Ala Gly Pro Lys Gly Ala Asp Gly Ala Pro
    1010                1015                1020

Gly Lys Asp Gly Val Arg Gly Leu Ala Gly Pro Ile Gly Pro Pro
    1025                1030                1035

Gly Glu Arg Gly Ala Ala Gly Leu Pro Gly Pro Lys Gly Glu Arg
```

```
                1040                1045                1050

Gly Asp  Ala Gly Pro Lys Gly  Ala Asp Gly Ala Pro  Gly Lys Asp
    1055                 1060                1065

Gly Val  Arg Gly Leu Ala Gly  Pro Ile Gly Pro Pro  Gly Pro Ala
    1070                 1075                1080

Gly Ala  Pro Gly Ala Pro Gly  Leu Gln Gly Met Pro  Gly Glu Arg
    1085                 1090                1095

Gly Ala  Ala Gly Leu Pro Gly  Pro Lys Gly Glu Arg  Gly Asp Ala
    1100                 1105                1110

Gly Pro  Lys Gly Ala Asp Gly  Ala Pro Gly Lys Asp  Gly Val Arg
    1115                 1120                1125

Gly Leu  Ala Gly Pro Pro
    1130

<210> SEQ ID NO 7
<211> LENGTH: 1323
<212> TYPE: PRT
<213> ORGANISM: Artificial
<220> FEATURE:
<223> OTHER INFORMATION: CBE7

<400> SEQUENCE: 7

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
                100                 105                 110

Pro Lys Gly Ala Asp Gly Ala Pro Gly Lys Asp Gly Val Arg Gly Leu
            115                 120                 125

Ala Gly Pro Ile Gly Pro Pro Gly Pro Ala Gly Ala Pro Gly Ala Pro
        130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
                180                 185                 190

Gly Leu Gln Gly Ala Pro Gly Leu Gln Gly Met Pro Gly Glu Arg Gly
            195                 200                 205

Ala Ala Gly Leu Pro Gly Pro Lys Gly Glu Arg Gly Asp Ala Gly Pro
        210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255

Asp Ala Gly Pro Lys Gly Ala Asp Gly Ala Pro Gly Lys Asp Gly Val
                260                 265                 270
```

-continued

```
Arg Gly Leu Ala Gly Pro Ile Gly Pro Pro Gly Glu Arg Gly Ala Ala
        275                 280                 285
Gly Leu Pro Gly Pro Lys Gly Glu Arg Gly Asp Ala Gly Pro Lys Gly
        290                 295                 300
Ala Asp Gly Ala Pro Gly Lys Asp Gly Val Arg Gly Leu Ala Gly Pro
305                 310                 315                 320
Ile Gly Pro Pro Gly Pro Ala Gly Ala Pro Gly Ala Pro Gly Leu Gln
                325                 330                 335
Gly Met Pro Gly Glu Arg Gly Ala Ala Gly Leu Pro Gly Pro Lys Gly
                340                 345                 350
Glu Arg Gly Asp Ala Gly Pro Lys Gly Ala Asp Gly Ala Pro Gly Lys
        355                 360                 365
Asp Gly Val Arg Gly Leu Ala Gly Pro Gly Ala Pro Gly Leu Gln
        370                 375                 380
Gly Ala Pro Gly Leu Gln Gly Met Pro Gly Glu Arg Gly Ala Ala Gly
385                 390                 395                 400
Leu Pro Gly Pro Lys Gly Glu Arg Gly Asp Ala Gly Pro Lys Gly Ala
                405                 410                 415
Asp Gly Ala Pro Gly Ala Pro Gly Leu Gln Gly Met Pro Gly Glu Arg
                420                 425                 430
Gly Ala Ala Gly Leu Pro Gly Pro Lys Gly Glu Arg Gly Asp Ala Gly
        435                 440                 445
Pro Lys Gly Ala Asp Gly Ala Pro Gly Lys Asp Gly Val Arg Gly Leu
450                 455                 460
Ala Gly Pro Ile Gly Pro Pro Gly Glu Arg Gly Ala Ala Gly Leu Pro
465                 470                 475                 480
Gly Pro Lys Gly Glu Arg Gly Asp Ala Gly Pro Lys Gly Ala Asp Gly
                485                 490                 495
Ala Pro Gly Lys Asp Gly Val Arg Gly Leu Ala Gly Pro Ile Gly Pro
                500                 505                 510
Pro Gly Pro Ala Gly Ala Pro Gly Ala Pro Gly Leu Gln Gly Met Pro
        515                 520                 525
Gly Glu Arg Gly Ala Ala Gly Leu Pro Gly Pro Lys Gly Glu Arg Gly
        530                 535                 540
Asp Ala Gly Pro Lys Gly Ala Asp Gly Ala Pro Gly Lys Asp Gly Val
545                 550                 555                 560
Arg Gly Leu Ala Gly Pro Pro Gly Ala Pro Gly Leu Gln Gly Ala Pro
                565                 570                 575
Gly Leu Gln Gly Met Pro Gly Glu Arg Gly Ala Ala Gly Leu Pro Gly
                580                 585                 590
Pro Lys Gly Glu Arg Gly Asp Ala Gly Pro Lys Gly Ala Asp Gly Ala
        595                 600                 605
Pro Gly Ala Pro Gly Leu Gln Gly Met Pro Gly Glu Arg Gly Ala Ala
        610                 615                 620
Gly Leu Pro Gly Pro Lys Gly Glu Arg Gly Asp Ala Gly Pro Lys Gly
625                 630                 635                 640
Ala Asp Gly Ala Pro Gly Lys Asp Gly Val Arg Gly Leu Ala Gly Pro
                645                 650                 655
Ile Gly Pro Pro Gly Glu Arg Gly Ala Ala Gly Leu Pro Gly Pro Lys
                660                 665                 670
Gly Glu Arg Gly Asp Ala Gly Pro Lys Gly Ala Asp Gly Ala Pro Gly
        675                 680                 685
Lys Asp Gly Val Arg Gly Leu Ala Gly Pro Ile Gly Pro Pro Gly Pro
```

```
                690             695             700
Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
            740                 745                 750

Ala Gly Pro Pro Gly Ala Pro Gly Leu Gln Gly Ala Pro Gly Leu Gln
                755                 760                 765

Gly Met Pro Gly Glu Arg Gly Ala Ala Gly Leu Pro Gly Pro Lys Gly
        770                 775                 780

Glu Arg Gly Asp Ala Gly Pro Lys Gly Ala Asp Gly Ala Pro Gly Ala
785                 790                 795                 800

Pro Gly Leu Gln Gly Met Pro Gly Glu Arg Gly Ala Ala Gly Leu Pro
                805                 810                 815

Gly Pro Lys Gly Glu Arg Gly Asp Ala Gly Pro Lys Gly Ala Asp Gly
            820                 825                 830

Ala Pro Gly Lys Asp Gly Val Arg Gly Leu Ala Gly Pro Ile Gly Pro
835                 840                 845

Pro Gly Glu Arg Gly Ala Ala Gly Leu Pro Gly Pro Lys Gly Glu Arg
            850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
                885                 890                 895

Pro Gly Ala Pro Gly Leu Gln Gly Met Pro Gly Glu Arg Gly Ala Ala
            900                 905                 910

Gly Leu Pro Gly Pro Lys Gly Glu Arg Gly Asp Ala Gly Pro Lys Gly
        915                 920                 925

Ala Asp Gly Ala Pro Gly Lys Asp Gly Val Arg Gly Leu Ala Gly Pro
930                 935                 940

Pro Gly Ala Pro Gly Leu Gln Gly Ala Pro Gly Leu Gln Gly Met Pro
945                 950                 955                 960

Gly Glu Arg Gly Ala Ala Gly Leu Pro Gly Pro Lys Gly Glu Arg Gly
            965                 970                 975

Asp Ala Gly Pro Lys Gly Ala Asp Gly Ala Pro Gly Ala Pro Gly Leu
            980                 985                 990

Gln Gly Met Pro Gly Glu Arg Gly Ala Ala Gly Leu Pro Gly Pro Lys
        995                 1000                1005

Gly Glu Arg Gly Asp Ala Gly Pro Lys Gly Ala Asp Gly Ala Pro
    1010                1015                1020

Gly Lys Asp Gly Val Arg Gly Leu Ala Gly Pro Ile Gly Pro Pro
    1025                1030                1035

Gly Glu Arg Gly Ala Ala Gly Leu Pro Gly Pro Lys Gly Glu Arg
    1040                1045                1050

Gly Asp Ala Gly Pro Lys Gly Ala Asp Gly Ala Pro Gly Lys Asp
    1055                1060                1065

Gly Val Arg Gly Leu Ala Gly Pro Ile Gly Pro Pro Gly Pro Ala
    1070                1075                1080

Gly Ala Pro Gly Ala Pro Gly Leu Gln Gly Met Pro Gly Glu Arg
    1085                1090                1095

Gly Ala Ala Gly Leu Pro Gly Pro Lys Gly Glu Arg Gly Asp Ala
    1100                1105                1110
```

-continued

Gly Pro Lys Gly Ala Asp Gly Ala Pro Gly Lys Asp Gly Val Arg
    1115                1120                1125

Gly Leu Ala Gly Pro Pro Gly Ala Pro Gly Leu Gln Gly Ala Pro
    1130                1135                1140

Gly Leu Gln Gly Met Pro Gly Glu Arg Gly Ala Ala Gly Leu Pro
    1145                1150                1155

Gly Pro Lys Gly Glu Arg Gly Asp Ala Gly Pro Lys Gly Ala Asp
    1160                1165                1170

Gly Ala Pro Gly Ala Pro Gly Leu Gln Gly Met Pro Gly Glu Arg
    1175                1180                1185

Gly Ala Ala Gly Leu Pro Gly Pro Lys Gly Glu Arg Gly Asp Ala
    1190                1195                1200

Gly Pro Lys Gly Ala Asp Gly Ala Pro Gly Lys Asp Gly Val Arg
    1205                1210                1215

Gly Leu Ala Gly Pro Ile Gly Pro Pro Gly Glu Arg Gly Ala Ala
    1220                1225                1230

Gly Leu Pro Gly Pro Lys Gly Glu Arg Gly Asp Ala Gly Pro Lys
    1235                1240                1245

Gly Ala Asp Gly Ala Pro Gly Lys Asp Gly Val Arg Gly Leu Ala
    1250                1255                1260

Gly Pro Ile Gly Pro Pro Gly Ala Gly Ala Pro Gly Ala Pro
    1265                1270                1275

Gly Leu Gln Gly Met Pro Gly Glu Arg Gly Ala Ala Gly Leu Pro
    1280                1285                1290

Gly Pro Lys Gly Glu Arg Gly Asp Ala Gly Pro Lys Gly Ala Asp
    1295                1300                1305

Gly Ala Pro Gly Lys Asp Gly Val Arg Gly Leu Ala Gly Pro Pro
    1310                1315                1320

<210> SEQ ID NO 8
<211> LENGTH: 1512
<212> TYPE: PRT
<213> ORGANISM: Artificial
<220> FEATURE:
<223> OTHER INFORMATION: CBE8

<400> SEQUENCE: 8

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly

```
            145                 150                 155                 160
        Pro Lys Gly Glu Arg Gly Asp Ala Gly Pro Lys Gly Ala Asp Gly Ala
                        165                 170                 175
        Pro Gly Lys Asp Gly Val Arg Gly Leu Ala Gly Pro Pro Gly Ala Pro
                        180                 185                 190
        Gly Leu Gln Gly Ala Pro Gly Leu Gln Gly Met Pro Gly Glu Arg Gly
                        195                 200                 205
        Ala Ala Gly Leu Pro Gly Pro Lys Gly Glu Arg Gly Asp Ala Gly Pro
                        210                 215                 220
        Lys Gly Ala Asp Gly Ala Pro Gly Ala Pro Gly Leu Gln Gly Met Pro
        225                 230                 235                 240
        Gly Glu Arg Gly Ala Ala Gly Leu Pro Gly Pro Lys Gly Glu Arg Gly
                        245                 250                 255
        Asp Ala Gly Pro Lys Gly Ala Asp Gly Ala Pro Gly Lys Asp Gly Val
                        260                 265                 270
        Arg Gly Leu Ala Gly Pro Ile Gly Pro Pro Gly Glu Arg Gly Ala Ala
                        275                 280                 285
        Gly Leu Pro Gly Pro Lys Gly Glu Arg Gly Asp Ala Gly Pro Lys Gly
                        290                 295                 300
        Ala Asp Gly Ala Pro Gly Lys Asp Gly Val Arg Gly Leu Ala Gly Pro
        305                 310                 315                 320
        Ile Gly Pro Pro Gly Pro Ala Gly Ala Pro Gly Ala Pro Gly Leu Gln
                        325                 330                 335
        Gly Met Pro Gly Glu Arg Gly Ala Ala Gly Leu Pro Gly Pro Lys Gly
                        340                 345                 350
        Glu Arg Gly Asp Ala Gly Pro Lys Gly Ala Asp Gly Ala Pro Gly Lys
                        355                 360                 365
        Asp Gly Val Arg Gly Leu Ala Gly Pro Pro Gly Ala Pro Gly Leu Gln
                        370                 375                 380
        Gly Ala Pro Gly Leu Gln Gly Met Pro Gly Glu Arg Gly Ala Ala Gly
        385                 390                 395                 400
        Leu Pro Gly Pro Lys Gly Glu Arg Gly Asp Ala Gly Pro Lys Gly Ala
                        405                 410                 415
        Asp Gly Ala Pro Gly Ala Pro Gly Leu Gln Gly Met Pro Gly Glu Arg
                        420                 425                 430
        Gly Ala Ala Gly Leu Pro Gly Pro Lys Gly Glu Arg Gly Asp Ala Gly
                        435                 440                 445
        Pro Lys Gly Ala Asp Gly Ala Pro Gly Lys Asp Gly Val Arg Gly Leu
        450                 455                 460
        Ala Gly Pro Ile Gly Pro Pro Gly Glu Arg Gly Ala Ala Gly Leu Pro
        465                 470                 475                 480
        Gly Pro Lys Gly Glu Arg Gly Asp Ala Gly Pro Lys Gly Ala Asp Gly
                        485                 490                 495
        Ala Pro Gly Lys Asp Gly Val Arg Gly Leu Ala Gly Pro Ile Gly Pro
                        500                 505                 510
        Pro Gly Pro Ala Gly Ala Pro Gly Ala Pro Gly Leu Gln Gly Met Pro
                        515                 520                 525
        Gly Glu Arg Gly Ala Ala Gly Leu Pro Gly Lys Gly Glu Arg Gly
                        530                 535                 540
        Asp Ala Gly Pro Lys Gly Ala Asp Gly Ala Pro Gly Lys Asp Gly Val
        545                 550                 555                 560
        Arg Gly Leu Ala Gly Pro Pro Gly Ala Pro Gly Leu Gln Gly Ala Pro
                        565                 570                 575
```

-continued

```
Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
        595                 600                 605

Pro Gly Ala Pro Gly Leu Gln Gly Met Pro Gly Glu Arg Gly Ala Ala
    610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
            645                 650                 655

Ile Gly Pro Pro Gly Glu Arg Gly Ala Ala Gly Leu Pro Gly Pro Lys
        660                 665                 670

Gly Glu Arg Gly Asp Ala Gly Pro Lys Gly Ala Asp Gly Ala Pro Gly
    675                 680                 685

Lys Asp Gly Val Arg Gly Leu Ala Gly Pro Ile Gly Pro Pro Gly Pro
    690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
            725                 730                 735

Pro Lys Gly Ala Asp Gly Ala Pro Gly Lys Asp Gly Val Arg Gly Leu
        740                 745                 750

Ala Gly Pro Pro Gly Ala Pro Gly Leu Gln Gly Ala Pro Gly Leu Gln
    755                 760                 765

Gly Met Pro Gly Glu Arg Gly Ala Ala Gly Leu Pro Gly Pro Lys Gly
    770                 775                 780

Glu Arg Gly Asp Ala Gly Pro Lys Gly Ala Asp Gly Ala Pro Gly Ala
785                 790                 795                 800

Pro Gly Leu Gln Gly Met Pro Gly Glu Arg Gly Ala Ala Gly Leu Pro
            805                 810                 815

Gly Pro Lys Gly Glu Arg Gly Asp Ala Gly Pro Lys Gly Ala Asp Gly
        820                 825                 830

Ala Pro Gly Lys Asp Gly Val Arg Gly Leu Ala Gly Pro Ile Gly Pro
    835                 840                 845

Pro Gly Glu Arg Gly Ala Ala Gly Leu Pro Gly Pro Lys Gly Glu Arg
    850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
            885                 890                 895

Pro Gly Ala Pro Gly Leu Gln Gly Met Pro Gly Glu Arg Gly Ala Ala
        900                 905                 910

Gly Leu Pro Gly Pro Lys Gly Glu Arg Gly Asp Ala Gly Pro Lys Gly
    915                 920                 925

Ala Asp Gly Ala Pro Gly Lys Asp Gly Val Arg Gly Leu Ala Gly Pro
    930                 935                 940

Pro Gly Ala Pro Gly Leu Gln Gly Ala Pro Gly Leu Gln Gly Met Pro
945                 950                 955                 960

Gly Glu Arg Gly Ala Ala Gly Leu Pro Gly Pro Lys Gly Glu Arg Gly
            965                 970                 975

Asp Ala Gly Pro Lys Gly Ala Asp Gly Ala Pro Gly Ala Pro Gly Leu
        980                 985                 990

Gln Gly Met Pro Gly Glu Arg Gly Ala Ala Gly Leu Pro Gly Pro Lys
    995                 1000                1005
```

```
Gly Glu  Arg Gly Asp Ala  Gly Pro Lys Gly Ala  Asp Gly Ala Pro
    1010             1015              1020

Gly Lys  Asp Gly Val Arg  Gly Leu Ala Gly Pro  Ile Gly Pro Pro
    1025             1030              1035

Gly Glu  Arg Gly Ala Ala  Gly Leu Pro Gly Pro  Lys Gly Glu Arg
    1040             1045              1050

Gly Asp  Ala Gly Pro Lys  Gly Ala Asp Gly Ala  Pro Gly Lys Asp
    1055             1060              1065

Gly Val  Arg Gly Leu Ala  Gly Pro Ile Gly Pro  Pro Gly Pro Ala
    1070             1075              1080

Gly Ala  Pro Gly Ala Pro  Gly Leu Gln Gly Met  Pro Gly Glu Arg
    1085             1090              1095

Gly Ala  Ala Gly Leu Pro  Gly Pro Lys Gly Glu  Arg Gly Asp Ala
    1100             1105              1110

Gly Pro  Lys Gly Ala Asp  Gly Ala Pro Gly Lys  Asp Gly Val Arg
    1115             1120              1125

Gly Leu  Ala Gly Pro Pro  Gly Ala Pro Gly Leu  Gln Gly Ala Pro
    1130             1135              1140

Gly Leu  Gln Gly Met Pro  Gly Glu Arg Gly Ala  Ala Gly Leu Pro
    1145             1150              1155

Gly Pro  Lys Gly Glu Arg  Gly Asp Ala Gly Pro  Lys Gly Ala Asp
    1160             1165              1170

Gly Ala  Pro Gly Ala Pro  Gly Leu Gln Gly Met  Pro Gly Glu Arg
    1175             1180              1185

Gly Ala  Ala Gly Leu Pro  Gly Pro Lys Gly Glu  Arg Gly Asp Ala
    1190             1195              1200

Gly Pro  Lys Gly Ala Asp  Gly Ala Pro Gly Lys  Asp Gly Val Arg
    1205             1210              1215

Gly Leu  Ala Gly Pro Ile  Gly Pro Pro Gly Glu  Arg Gly Ala Ala
    1220             1225              1230

Gly Leu  Pro Gly Pro Lys  Gly Glu Arg Gly Asp  Ala Gly Pro Lys
    1235             1240              1245

Gly Ala  Asp Gly Ala Pro  Gly Lys Asp Gly Val  Arg Gly Leu Ala
    1250             1255              1260

Gly Pro  Ile Gly Pro Pro  Gly Ala Gly Ala Pro  Gly Ala Pro
    1265             1270              1275

Gly Leu  Gln Gly Met Pro  Gly Glu Arg Gly Ala  Ala Gly Leu Pro
    1280             1285              1290

Gly Pro  Lys Gly Glu Arg  Gly Asp Ala Gly Pro  Lys Gly Ala Asp
    1295             1300              1305

Gly Ala  Pro Gly Lys Asp  Gly Val Arg Gly Leu  Ala Gly Pro Pro
    1310             1315              1320

Gly Ala  Pro Gly Leu Gln  Gly Ala Pro Gly Leu  Gln Gly Met Pro
    1325             1330              1335

Gly Glu  Arg Gly Ala Ala  Gly Leu Pro Gly Pro  Lys Gly Glu Arg
    1340             1345              1350

Gly Asp  Ala Gly Pro Lys  Gly Ala Asp Gly Ala  Pro Gly Ala Pro
    1355             1360              1365

Gly Leu  Gln Gly Met Pro  Gly Glu Arg Gly Ala  Ala Gly Leu Pro
    1370             1375              1380

Gly Pro  Lys Gly Glu Arg  Gly Asp Ala Gly Pro  Lys Gly Ala Asp
    1385             1390              1395

Gly Ala  Pro Gly Lys Asp  Gly Val Arg Gly Leu  Ala Gly Pro Ile
```

```
                    1400                1405                1410

Gly Pro Pro Gly Glu Arg Gly Ala Ala Gly Leu Pro Gly Pro Lys
    1415                1420                1425

Gly Glu Arg Gly Asp Ala Gly Pro Lys Gly Ala Asp Gly Ala Pro
    1430                1435                1440

Gly Lys Asp Gly Val Arg Gly Leu Ala Gly Pro Ile Gly Pro Pro
    1445                1450                1455

Gly Pro Ala Gly Ala Pro Gly Ala Pro Gly Leu Gln Gly Met Pro
    1460                1465                1470

Gly Glu Arg Gly Ala Ala Gly Leu Pro Gly Pro Lys Gly Glu Arg
    1475                1480                1485

Gly Asp Ala Gly Pro Lys Gly Ala Asp Gly Ala Pro Gly Lys Asp
    1490                1495                1500

Gly Val Arg Gly Leu Ala Gly Pro Pro
    1505                1510

<210> SEQ ID NO 9
<211> LENGTH: 1701
<212> TYPE: PRT
<213> ORGANISM: Artificial
<220> FEATURE:
<223> OTHER INFORMATION: CBE9

<400> SEQUENCE: 9

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Ala Gly Pro
    210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255
```

```
Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
            275                 280                 285

Gly Leu Pro Gly Pro Lys Gly Glu Arg Gly Asp Ala Gly Pro Lys Gly
            290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
            355                 360                 365

Asp Gly Val Arg Gly Leu Ala Gly Pro Pro Gly Ala Pro Gly Leu Gln
            370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
                405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
            435                 440                 445

Pro Lys Gly Ala Asp Gly Ala Pro Gly Lys Asp Gly Val Arg Gly Leu
            450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
            530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
                565                 570                 575

Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
            595                 600                 605

Pro Gly Ala Pro Gly Leu Gln Gly Met Pro Gly Glu Arg Gly Ala Ala
            610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655

Ile Gly Pro Pro Gly Glu Arg Gly Ala Ala Gly Leu Pro Gly Pro Lys
            660                 665                 670

Gly Glu Arg Gly Asp Ala Gly Pro Lys Gly Ala Asp Gly Ala Pro Gly
```

```
                    675                 680                 685
Lys Asp Gly Val Arg Gly Leu Ala Gly Pro Ile Gly Pro Gly Pro
690                     695                 700
Ala Gly Ala Pro Gly Ala Pro Gly Leu Gln Gly Met Pro Gly Glu Arg
705                 710                 715                 720
Gly Ala Ala Gly Leu Pro Gly Pro Lys Gly Glu Arg Gly Asp Ala Gly
                    725                 730                 735
Pro Lys Gly Ala Asp Gly Ala Pro Gly Lys Asp Gly Val Arg Gly Leu
                740                 745                 750
Ala Gly Pro Pro Gly Ala Pro Gly Leu Gln Gly Ala Pro Gly Leu Gln
            755                 760                 765
Gly Met Pro Gly Glu Arg Gly Ala Ala Gly Leu Pro Gly Pro Lys Gly
        770                 775                 780
Glu Arg Gly Asp Ala Gly Pro Lys Gly Ala Asp Gly Ala Pro Gly Ala
785                 790                 795                 800
Pro Gly Leu Gln Gly Met Pro Gly Glu Arg Gly Ala Ala Gly Leu Pro
                    805                 810                 815
Gly Pro Lys Gly Glu Arg Gly Asp Ala Gly Pro Lys Gly Ala Asp Gly
                    820                 825                 830
Ala Pro Gly Lys Asp Gly Val Arg Gly Leu Ala Gly Pro Ile Gly Pro
            835                 840                 845
Pro Gly Glu Arg Gly Ala Ala Gly Leu Pro Gly Pro Lys Gly Glu Arg
850                 855                 860
Gly Asp Ala Gly Pro Lys Gly Ala Asp Gly Ala Pro Gly Lys Asp Gly
865                 870                 875                 880
Val Arg Gly Leu Ala Gly Pro Ile Gly Pro Pro Gly Pro Ala Gly Ala
                885                 890                 895
Pro Gly Ala Pro Gly Leu Gln Gly Met Pro Gly Glu Arg Gly Ala Ala
            900                 905                 910
Gly Leu Pro Gly Pro Lys Gly Glu Arg Gly Asp Ala Gly Pro Lys Gly
        915                 920                 925
Ala Asp Gly Ala Pro Gly Lys Asp Gly Val Arg Gly Leu Ala Gly Pro
930                 935                 940
Pro Gly Ala Pro Gly Leu Gln Gly Ala Pro Gly Leu Gln Gly Met Pro
945                 950                 955                 960
Gly Glu Arg Gly Ala Ala Gly Leu Pro Gly Pro Lys Gly Glu Arg Gly
                965                 970                 975
Asp Ala Gly Pro Lys Gly Ala Asp Gly Ala Pro Gly Ala Pro Gly Leu
            980                 985                 990
Gln Gly Met Pro Gly Glu Arg Gly Ala Ala Gly Leu Pro Gly Pro Lys
        995                 1000                1005
Gly Glu Arg Gly Asp Ala Gly Pro Lys Gly Ala Asp Gly Ala Pro
    1010                1015                1020
Gly Lys Asp Gly Val Arg Gly Leu Ala Gly Pro Ile Gly Pro Pro
    1025                1030                1035
Gly Glu Arg Gly Ala Ala Gly Leu Pro Gly Pro Lys Gly Glu Arg
    1040                1045                1050
Gly Asp Ala Gly Pro Lys Gly Ala Asp Gly Ala Pro Gly Lys Asp
    1055                1060                1065
Gly Val Arg Gly Leu Ala Gly Pro Ile Gly Pro Pro Gly Pro Ala
    1070                1075                1080
Gly Ala Pro Gly Ala Pro Gly Leu Gln Gly Met Pro Gly Glu Arg
    1085                1090                1095
```

```
Gly Ala Ala Gly Leu Pro Gly Pro Lys Gly Glu Arg Gly Asp Ala
        1100                1105                1110

Gly Pro Lys Gly Ala Asp Gly Ala Pro Gly Lys Asp Gly Val Arg
    1115                1120                1125

Gly Leu Ala Gly Pro Pro Gly Ala Pro Gly Leu Gln Gly Ala Pro
    1130                1135                1140

Gly Leu Gln Gly Met Pro Gly Glu Arg Gly Ala Ala Gly Leu Pro
    1145                1150                1155

Gly Pro Lys Gly Glu Arg Gly Asp Ala Gly Pro Lys Gly Ala Asp
    1160                1165                1170

Gly Ala Pro Gly Ala Pro Gly Leu Gln Gly Met Pro Gly Glu Arg
    1175                1180                1185

Gly Ala Ala Gly Leu Pro Gly Pro Lys Gly Glu Arg Gly Asp Ala
    1190                1195                1200

Gly Pro Lys Gly Ala Asp Gly Ala Pro Gly Lys Asp Gly Val Arg
    1205                1210                1215

Gly Leu Ala Gly Pro Ile Gly Pro Pro Gly Glu Arg Gly Ala Ala
    1220                1225                1230

Gly Leu Pro Gly Pro Lys Gly Glu Arg Gly Asp Ala Gly Pro Lys
    1235                1240                1245

Gly Ala Asp Gly Ala Pro Gly Lys Asp Gly Val Arg Gly Leu Ala
    1250                1255                1260

Gly Pro Ile Gly Pro Pro Gly Ala Gly Ala Pro Gly Ala Pro
    1265                1270                1275

Gly Leu Gln Gly Met Pro Gly Glu Arg Gly Ala Ala Gly Leu Pro
    1280                1285                1290

Gly Pro Lys Gly Glu Arg Gly Asp Ala Gly Pro Lys Gly Ala Asp
    1295                1300                1305

Gly Ala Pro Gly Lys Asp Gly Val Arg Gly Leu Ala Gly Pro Pro
    1310                1315                1320

Gly Ala Pro Gly Leu Gln Gly Ala Pro Gly Leu Gln Gly Met Pro
    1325                1330                1335

Gly Glu Arg Gly Ala Ala Gly Leu Pro Gly Pro Lys Gly Glu Arg
    1340                1345                1350

Gly Asp Ala Gly Pro Lys Gly Ala Asp Gly Ala Pro Gly Ala Pro
    1355                1360                1365

Gly Leu Gln Gly Met Pro Gly Glu Arg Gly Ala Ala Gly Leu Pro
    1370                1375                1380

Gly Pro Lys Gly Glu Arg Gly Asp Ala Gly Pro Lys Gly Ala Asp
    1385                1390                1395

Gly Ala Pro Gly Lys Asp Gly Val Arg Gly Leu Ala Gly Pro Ile
    1400                1405                1410

Gly Pro Pro Gly Glu Arg Gly Ala Ala Gly Leu Pro Gly Pro Lys
    1415                1420                1425

Gly Glu Arg Gly Asp Ala Gly Pro Lys Gly Ala Asp Gly Ala Pro
    1430                1435                1440

Gly Lys Asp Gly Val Arg Gly Leu Ala Gly Pro Ile Gly Pro Pro
    1445                1450                1455

Gly Pro Ala Gly Ala Pro Gly Ala Pro Gly Leu Gln Gly Met Pro
    1460                1465                1470

Gly Glu Arg Gly Ala Ala Gly Leu Pro Gly Pro Lys Gly Glu Arg
    1475                1480                1485

Gly Asp Ala Gly Pro Lys Gly Ala Asp Gly Ala Pro Gly Lys Asp
    1490                1495                1500
```

```
Gly Val Arg Gly Leu Ala Gly Pro Pro Gly Ala Pro Gly Leu Gln
    1505                1510                1515

Gly Ala Pro Gly Leu Gln Gly Met Pro Gly Glu Arg Gly Ala Ala
    1520                1525                1530

Gly Leu Pro Gly Pro Lys Gly Glu Arg Gly Asp Ala Gly Pro Lys
    1535                1540                1545

Gly Ala Asp Gly Ala Pro Gly Ala Pro Gly Leu Gln Gly Met Pro
    1550                1555                1560

Gly Glu Arg Gly Ala Ala Gly Leu Pro Gly Pro Lys Gly Glu Arg
    1565                1570                1575

Gly Asp Ala Gly Pro Lys Gly Ala Asp Gly Ala Pro Gly Lys Asp
    1580                1585                1590

Gly Val Arg Gly Leu Ala Gly Pro Ile Gly Pro Pro Gly Glu Arg
    1595                1600                1605

Gly Ala Ala Gly Leu Pro Gly Pro Lys Gly Glu Arg Gly Asp Ala
    1610                1615                1620

Gly Pro Lys Gly Ala Asp Gly Ala Pro Gly Lys Asp Gly Val Arg
    1625                1630                1635

Gly Leu Ala Gly Pro Ile Gly Pro Pro Gly Pro Ala Gly Ala Pro
    1640                1645                1650

Gly Ala Pro Gly Leu Gln Gly Met Pro Gly Glu Arg Gly Ala Ala
    1655                1660                1665

Gly Leu Pro Gly Pro Lys Gly Glu Arg Gly Asp Ala Gly Pro Lys
    1670                1675                1680

Gly Ala Asp Gly Ala Pro Gly Lys Asp Gly Val Arg Gly Leu Ala
    1685                1690                1695

Gly Pro Pro
    1700

<210> SEQ ID NO 10
<211> LENGTH: 1890
<212> TYPE: PRT
<213> ORGANISM: Artificial
<220> FEATURE:
<223> OTHER INFORMATION: CBE10

<400> SEQUENCE: 10

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140
```

```
Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
            165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
            195                 200                 205

Ala Ala Gly Leu Pro Gly Pro Lys Gly Glu Arg Gly Asp Ala Gly Pro
210                 215                 220

Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
            245                 250                 255

Asp Ala Gly Pro Lys Gly Ala Asp Gly Ala Pro Gly Lys Asp Gly Val
            260                 265                 270

Arg Gly Leu Ala Gly Pro Ile Gly Pro Pro Gly Glu Arg Gly Ala Ala
            275                 280                 285

Gly Leu Pro Gly Pro Lys Gly Glu Arg Gly Asp Ala Gly Pro Lys Gly
            290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
            325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
            355                 360                 365

Asp Gly Val Arg Gly Leu Ala Gly Pro Pro Gly Ala Pro Gly Leu Gln
            370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
            405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
            435                 440                 445

Pro Lys Gly Ala Asp Gly Ala Pro Gly Lys Asp Gly Val Arg Gly Leu
450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
            485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
            530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
            565                 570                 575
```

```
Gly Leu Gln Gly Met Pro Gly Glu Arg Gly Ala Ala Gly Leu Pro Gly
                580                 585                 590

Pro Lys Gly Glu Arg Gly Asp Ala Gly Pro Lys Gly Ala Asp Gly Ala
            595                 600             605

Pro Gly Ala Pro Gly Leu Gln Gly Met Pro Gly Glu Arg Gly Ala Ala
        610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655

Ile Gly Pro Pro Gly Glu Arg Gly Ala Ala Gly Leu Pro Gly Pro Lys
            660                 665                 670

Gly Glu Arg Gly Asp Ala Gly Pro Lys Gly Ala Asp Gly Ala Pro Gly
        675                 680                 685

Lys Asp Gly Val Arg Gly Leu Ala Gly Pro Ile Gly Pro Pro Gly Pro
690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
            740                 745                 750

Ala Gly Pro Pro Gly Ala Pro Gly Leu Gln Gly Ala Pro Gly Leu Gln
        755                 760                 765

Gly Met Pro Gly Glu Arg Gly Ala Ala Gly Leu Pro Gly Pro Lys Gly
        770                 775                 780

Glu Arg Gly Asp Ala Gly Pro Lys Gly Ala Asp Gly Ala Pro Gly Ala
785                 790                 795                 800

Pro Gly Leu Gln Gly Met Pro Gly Glu Arg Gly Ala Ala Gly Leu Pro
                805                 810                 815

Gly Pro Lys Gly Glu Arg Gly Asp Ala Gly Pro Lys Gly Ala Asp Gly
            820                 825                 830

Ala Pro Gly Lys Asp Gly Val Arg Gly Leu Ala Gly Pro Ile Gly Pro
        835                 840                 845

Pro Gly Glu Arg Gly Ala Ala Gly Leu Pro Gly Pro Lys Gly Glu Arg
        850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
                885                 890                 895

Pro Gly Ala Pro Gly Leu Gln Gly Met Pro Gly Glu Arg Gly Ala Ala
            900                 905                 910

Gly Leu Pro Gly Pro Lys Gly Glu Arg Gly Asp Ala Gly Pro Lys Gly
        915                 920                 925

Ala Asp Gly Ala Pro Gly Lys Asp Gly Val Arg Gly Leu Ala Gly Pro
        930                 935                 940

Pro Gly Ala Pro Gly Leu Gln Gly Ala Pro Gly Leu Gln Gly Met Pro
945                 950                 955                 960

Gly Glu Arg Gly Ala Ala Gly Leu Pro Gly Pro Lys Gly Glu Arg Gly
                965                 970                 975

Asp Ala Gly Pro Lys Gly Ala Asp Gly Ala Pro Gly Ala Pro Gly Leu
            980                 985                 990

Gln Gly Met Pro Gly Glu Arg Gly  Ala Ala Gly Leu Pro  Gly Pro Lys
```

```
                995                 1000                1005
Gly Glu Arg Gly Asp Ala Gly Pro Lys Gly Ala Asp Gly Ala Pro
    1010                1015                1020

Gly Lys Asp Gly Val Arg Gly Leu Ala Gly Pro Ile Gly Pro Pro
    1025                1030                1035

Gly Glu Arg Gly Ala Ala Gly Leu Pro Gly Pro Lys Gly Glu Arg
    1040                1045                1050

Gly Asp Ala Gly Pro Lys Gly Ala Asp Gly Ala Pro Gly Lys Asp
    1055                1060                1065

Gly Val Arg Gly Leu Ala Gly Pro Ile Gly Pro Pro Gly Pro Ala
    1070                1075                1080

Gly Ala Pro Gly Ala Pro Gly Leu Gln Gly Met Pro Gly Glu Arg
    1085                1090                1095

Gly Ala Ala Gly Leu Pro Gly Pro Lys Gly Glu Arg Gly Asp Ala
    1100                1105                1110

Gly Pro Lys Gly Ala Asp Gly Ala Pro Gly Lys Asp Gly Val Arg
    1115                1120                1125

Gly Leu Ala Gly Pro Pro Gly Ala Pro Gly Leu Gln Gly Ala Pro
    1130                1135                1140

Gly Leu Gln Gly Met Pro Gly Glu Arg Gly Ala Ala Gly Leu Pro
    1145                1150                1155

Gly Pro Lys Gly Glu Arg Gly Asp Ala Gly Pro Lys Gly Ala Asp
    1160                1165                1170

Gly Ala Pro Gly Ala Pro Gly Leu Gln Gly Met Pro Gly Glu Arg
    1175                1180                1185

Gly Ala Ala Gly Leu Pro Gly Pro Lys Gly Glu Arg Gly Asp Ala
    1190                1195                1200

Gly Pro Lys Gly Ala Asp Gly Ala Pro Gly Lys Asp Gly Val Arg
    1205                1210                1215

Gly Leu Ala Gly Pro Ile Gly Pro Pro Gly Glu Arg Gly Ala Ala
    1220                1225                1230

Gly Leu Pro Gly Pro Lys Gly Glu Arg Gly Asp Ala Gly Pro Lys
    1235                1240                1245

Gly Ala Asp Gly Ala Pro Gly Lys Asp Gly Val Arg Gly Leu Ala
    1250                1255                1260

Gly Pro Ile Gly Pro Pro Gly Pro Ala Gly Ala Pro Gly Ala Pro
    1265                1270                1275

Gly Leu Gln Gly Met Pro Gly Glu Arg Gly Ala Ala Gly Leu Pro
    1280                1285                1290

Gly Pro Lys Gly Glu Arg Gly Asp Ala Gly Pro Lys Gly Ala Asp
    1295                1300                1305

Gly Ala Pro Gly Lys Asp Gly Val Arg Gly Leu Ala Gly Pro Pro
    1310                1315                1320

Gly Ala Pro Gly Leu Gln Gly Ala Pro Gly Leu Gln Gly Met Pro
    1325                1330                1335

Gly Glu Arg Gly Ala Ala Gly Leu Pro Gly Pro Lys Gly Glu Arg
    1340                1345                1350

Gly Asp Ala Gly Pro Lys Gly Ala Asp Gly Ala Pro Gly Ala Pro
    1355                1360                1365

Gly Leu Gln Gly Met Pro Gly Glu Arg Gly Ala Ala Gly Leu Pro
    1370                1375                1380

Gly Pro Lys Gly Glu Arg Gly Asp Ala Gly Pro Lys Gly Ala Asp
    1385                1390                1395
```

-continued

```
Gly Ala  Pro Gly Lys Asp Gly Val Arg Gly Leu Ala  Gly Pro Ile
    1400              1405             1410

Gly Pro  Pro Gly Glu Arg Gly Ala Ala Gly Leu Pro  Gly Pro Lys
    1415              1420             1425

Gly Glu  Arg Gly Asp Ala Gly Pro Lys Gly Ala Asp  Gly Ala Pro
    1430              1435             1440

Gly Lys  Asp Gly Val Arg Gly Leu Ala Gly Pro Ile  Gly Pro Pro
    1445              1450             1455

Gly Pro  Ala Gly Ala Pro Gly Ala Pro Gly Leu Gln  Gly Met Pro
    1460              1465             1470

Gly Glu  Arg Gly Ala Ala Gly Leu Pro Gly Pro Lys  Gly Glu Arg
    1475              1480             1485

Gly Asp  Ala Gly Pro Lys Gly Ala Asp Gly Ala Pro  Gly Lys Asp
    1490              1495             1500

Gly Val  Arg Gly Leu Ala Gly Pro Pro Gly Ala Pro  Gly Leu Gln
    1505              1510             1515

Gly Ala  Pro Gly Leu Gln Gly Met Pro Gly Glu Arg  Gly Ala Ala
    1520              1525             1530

Gly Leu  Pro Gly Pro Lys Gly Glu Arg Gly Asp Ala  Gly Pro Lys
    1535              1540             1545

Gly Ala  Asp Gly Ala Pro Gly Ala Pro Gly Leu Gln  Gly Met Pro
    1550              1555             1560

Gly Glu  Arg Gly Ala Ala Gly Leu Pro Gly Pro Lys  Gly Glu Arg
    1565              1570             1575

Gly Asp  Ala Gly Pro Lys Gly Ala Asp Gly Ala Pro  Gly Lys Asp
    1580              1585             1590

Gly Val  Arg Gly Leu Ala Gly Pro Ile Gly Pro Pro  Gly Glu Arg
    1595              1600             1605

Gly Ala  Ala Gly Leu Pro Gly Pro Lys Gly Glu Arg  Gly Asp Ala
    1610              1615             1620

Gly Pro  Lys Gly Ala Asp Gly Ala Pro Gly Lys Asp  Gly Val Arg
    1625              1630             1635

Gly Leu  Ala Gly Pro Ile Gly Pro Pro Gly Pro Ala  Gly Ala Pro
    1640              1645             1650

Gly Ala  Pro Gly Leu Gln Gly Met Pro Gly Glu Arg  Gly Ala Ala
    1655              1660             1665

Gly Leu  Pro Gly Pro Lys Gly Glu Arg Gly Asp Ala  Gly Pro Lys
    1670              1675             1680

Gly Ala  Asp Gly Ala Pro Gly Lys Asp Gly Val Arg  Gly Leu Ala
    1685              1690             1695

Gly Pro  Pro Gly Ala Pro Gly Leu Gln Gly Ala Pro  Gly Leu Gln
    1700              1705             1710

Gly Met  Pro Gly Glu Arg Gly Ala Ala Gly Leu Pro  Gly Pro Lys
    1715              1720             1725

Gly Glu  Arg Gly Asp Ala Gly Pro Lys Gly Ala Asp  Gly Ala Pro
    1730              1735             1740

Gly Ala  Pro Gly Leu Gln Gly Met Pro Gly Glu Arg  Gly Ala Ala
    1745              1750             1755

Gly Leu  Pro Gly Pro Lys Gly Glu Arg Gly Asp Ala  Gly Pro Lys
    1760              1765             1770

Gly Ala  Asp Gly Ala Pro Gly Lys Asp Gly Val Arg  Gly Leu Ala
    1775              1780             1785

Gly Pro  Ile Gly Pro Pro Gly Glu Arg Gly Ala Ala  Gly Leu Pro
    1790              1795             1800
```

```
Gly Pro Lys Gly Glu Arg Gly Asp Ala Gly Pro Lys Gly Ala Asp
    1805            1810                1815

Gly Ala Pro Gly Lys Asp Gly Val Arg Gly Leu Ala Gly Pro Ile
    1820            1825                1830

Gly Pro Pro Gly Pro Ala Gly Ala Pro Gly Ala Pro Gly Leu Gln
    1835            1840                1845

Gly Met Pro Gly Glu Arg Gly Ala Ala Gly Leu Pro Gly Pro Lys
    1850            1855                1860

Gly Glu Arg Gly Asp Ala Gly Pro Lys Gly Ala Asp Gly Ala Pro
    1865            1870                1875

Gly Lys Asp Gly Val Arg Gly Leu Ala Gly Pro Pro
    1880            1885                1890

<210> SEQ ID NO 11
<211> LENGTH: 192
<212> TYPE: PRT
<213> ORGANISM: Artificial
<220> FEATURE:
<223> OTHER INFORMATION: CBE

<400> SEQUENCE: 11

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Ile
            180                 185                 190
```

RECOMBINANT GELATINS

This application is a divisional of U.S. patent application Ser. No. 12/527,900, filed Aug. 20, 2009, which is a national stage of International Patent Application PCT/NL08/050098, filed Feb. 21, 2008, which claims priority to European Patent Applications 07102839.3, 07102838.5, filed Feb. 21, 2007, 07116189.7, 07116193.9, filed Sep. 12, 2007, and 08100556.3, filed Jan. 16, 2008, all of which are incorporated by reference herein in the entirety.

FIELD OF THE INVENTION

The invention is in the field of recombinantly produced gelatins. The gelatins of the present invention are of particular use in several applications involving cell attachment such as in cell culture work and applications involving cell cultures of anchor dependent cells and also in a variety of medical applications.

BACKGROUND OF THE INVENTION

Cell culture systems of animal cells, in particular mammalian cells (including human cells), is important for the production of many important (genetically engineered) biological materials such as vaccines, enzymes, hormones and antibodies. The majority of animal cells are anchorage-dependent and require attachment to a surface or cell culture support for their survival and growth.

Cell attachment also plays an important role in medical applications such as wound treatment (including artificial skin materials), bone and cartilage (re)growth and implantations and artificial blood vessel materials. Thus in medical applications often the demand is that a material, such as an implant or transplant material, comprises a biocompatible coating in terms of cell attachment.

Another area of interest in relation to cell attachment is the blocking of attachment receptors of cells. For instance by blocking the attachment receptors cancer metastasis may be influenced or inhibited, platelet aggregation may be influenced in antithrombotic compositions and tissues adhesion may be prevented, e.g. after surgery, or may be promoted, e.g. for dental products or other medical products.

In US 2006/0241032 RGD-enriched gelatin-like proteins with a minimum (increased) level of RGD motifs and with a certain distribution of said RGD motifs are disclosed that were found to be highly suitable for cell adhesion and cell binding in medical and biotechnological applications. The cell binding peptides described therein have good cell attachment properties.

There is however always the need for further improvements of materials for use in applications involving cell attachment. The instant invention provides improved gelatine-like polypeptides, which are particularly useful for cell attachment.

SUMMARY OF THE INVENTION

In the search for further improvements of gelatins that are enriched in RGD motifs that are suitable for cell adhesion and cell attachment, the present inventors identified a particularly advantageous gelatin. It is a recombinant gelatin comprising or consisting of a sequence with at least 75%, preferably at least 95%, sequence identity to SEQ ID NO: 1. This SEQ ID NO: 1 is also identified as "CBE monomer" or "$CBE_1$" and comprises 4 RGD motifs. Also multimers could be made comprising mentioned monomer which multimers are referred to "$CBE_x$" (wherein x=2-10), having very good polypeptide stability and cell adhesive properties. The multimers have the advantage that they are typically produced in significantly higher yields than the monomer. For instance, yields obtained for the CBE monomer are typically 3-5 gram per liter clarified broth, whereas CBE multimers were produced in amounts exceeding 10 g/l. Thus, in one embodiment of the invention, the recombinant gelatins are provided, as well as cell supports coated therewith and controlled release compositions comprising the recombinant gelatins. Also methods for using the recombinant gelatins and/or the cell supports or controlled release compositions for cell adhesion related medical applications are provided.

GENERAL DEFINITIONS

Whereas often the terms 'collagen', 'collagen-related', 'collagen-derived' or the like are also used in the art, the term 'gelatin' or 'gelatin-like' protein will be used throughout the rest of this description. Natural gelatin is a mixture of individual polymers with MW's ranging from 5,000 up to more than 400,000 daltons.

The terms "cell adhesion" and "cell attachment" are used interchangeably.

Also the terms "RGD sequence" and "RGD motif" are used interchangeably.

The terms "protein" or "polypeptide" or "peptide" are used interchangeably and refer to molecules consisting of a chain of amino acids, without reference to a specific mode of action, size, 3-dimensional structure or origin.

The term "support" or "cell attachment support" refers herein to any support which can be used to facilitate cell attachment and/or growth, such as culture dishes, microcarriers (e.g. microcarrier beads), stents, implants, etc.

The term "substantially identical", "substantial identity" or "essentially similar" or "essential similarity" means that two polypeptide, when aligned pairwise using the Smith-Waterman algorithm with default parameters, comprise at least 76%, 77% or 78%, preferably at least 80%, more preferably at least 85%, 90%, 95%, 98%, 99% or more amino acid sequence identity. More preferably, the polypeptides comprise said amino acid sequence identity while having no more than 3 gaps, preferably no more than 2 gaps, even more preferably no more than 1 gap and most preferably 0 gaps in the alignment. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or using in EmbossWIN (e.g. version 2.10.0). For comparing sequence identity between two sequences, it is preferred that local alignment algorithms are used, such as the Smith Waterman algorithm (Smith T F, Waterman M S (1981) J. Mol. Biol 147(1);195-7), used e.g. in the EmbossWIN program "water". Default parameters are gap opening penalty 10.0 and gap extension penalty 0.5, using the Blosum62 substitution matrix for proteins (Henikoff & Henikoff, 1992, PNAS 89, 915-919).

The term "comprising" is to be interpreted as specifying the presence of the stated parts, steps or components, but does not exclude the presence of one or more additional parts, steps or components.

In addition, reference to an element by the indefinite article "a" or "an" does not exclude the possibility that more than one of the element is present, unless the context clearly requires that there be one and only one of the elements. The indefinite article "a" or "an" thus usually means "at least one".

"Monomer" refers to a polypeptide unit which can be used to generate a "multimer" by repeating the unit in a linear fashion to generate a longer polypeptide. The monomer units are preferably repeated without intervening amino acids, although optionally 1, 2, 3, 4 or 5 linking amino acids may be present between monomer units.

DETAILED DESCRIPTION OF THE INVENTION

The present invention is directed to peptides, polypeptides or proteins, in particular to gelatines or gelatine-like proteins, which are highly suitable for cell adhesion and can be used in medical or biotechnological applications. More specifically the invention is directed to cell binding peptides or polypeptides that have improved properties compared to known recombinant gelatine-like RGD-comprising polypeptides, such as described in US 2006/0241032, in particular the sequence designated as SEQ ID NO: 2 therein.

It was found, surprisingly, that it is possible to obtain improved peptides or polypeptides with excellent cell attachment properties and high production yield, which comprise advantages such as improved stability, improved cell attachment properties (probably due to the improved stability) and/or result in a more homogenous distribution of particle size of carriers coated with the recombinant polypeptides (such as core microcarrier beads).

The polypeptides also do not display any health related risks, as they have a low antigenicity and that they can be used without the risk of transferring pathological factors such as viruses, prions and the like.

Without limiting the invention, it is thought that not only the distribution and amount of RGD motifs is important in determining the properties of the polypeptides, For example, in addition to the cell attachment properties, the stability and/or 3-dimensional folding of the polypeptides is an important factor which determines the usefulness of the polypeptide. In this aspect, it was found that not only the number of RGD motifs and their distribution, but that also the intervening amino acid sequences may contribute to the improved properties. Although the monomer CBE polypeptide according to the invention has some sequence similarity to e.g. SEQ ID NO: 2 of US2006/0241032, and also comprises 4 RGD motifs, it is still substantially different from that sequence. When aligned, the two polypeptides have only 72.8% sequence identity and also contain a large number of gaps in the alignment (54 gaps, i.e. 54 unmatched amino acids). Especially one of the amino acids next to each of the RGD sequences is E in the polypeptides according to the invention (i.e. ERGD), while it is D in the polypeptide described in the US patent application (DRGD). Also, the spacing between the RGD motifs is shorter in the monomer (and multimers) according to the invention, with at most 54 amino acids between RGDs (33, 39 and 54 amino acids between the first and second, second and third, and third and fourth RGD, respectively), while the prior art sequence comprises 60 amino acids between RGDs. These features are believed to contribute to the improved properties of the instant polypeptides.

Gelatin Like Polypeptide Monomers According to the Invention

Thus, in one embodiment a recombinant gelatine like protein is provided comprising or consisting of an amino acid sequence having at least 75% amino acid sequence identity to SEQ ID NO: 1, more preferably at least 76%, 78%, 80%, 85%, 90%, 95%, 96%, 98%, 99% sequence identity. Preferably said sequence comprises at least 4 RGD motifs, in particular, at least 1, 2, 3 or 4 ERGD motifs. Preferably, the RGD and/or ERGD motifs are distributed relatively evenly within the sequence, with at least about 30, 35, 40, 45 or 50 amino acids between, but preferably there are not more than about 100 amino acids, more preferably less than 60, more preferably not more than 55 amino acids between two RGD and/or ERGD motifs. In one embodiment the recombinant gelatine like protein comprises at least three RGD and/or ERGD motifs wherein the number of amino acids between sequentially a first and second RGD and/or ERGD motif is different from the number of amino acids between said second and sequentially a third RGD and/or ERGD motif. In one embodiment the polypeptide comprises preferably at least 4 RGD and/or ERGD motifs per 100, 150, 200 or 212 amino acids. Optionally more RGD and/or ERGD motifs may be present, such as 5, 6 or 7.

In one embodiment the recombinant gelatine like protein comprises or consists of the monomer of SEQ ID NO: 1 ($CBE_1$) or a variant thereof, such as an amino acid sequence comprising the above % amino acid sequence identity to SEQ ID NO: 1.

The gelatine like protein monomer preferably comprises a substantial number, or consists of GXY triads, wherein G is Glycine and X and Y are any amino acid. A substantial number of GXY triads refers to at least about 50%, more preferably at least 60%, 70%, 80%, 90% or most preferably 100% of amino acid triplets being GXY. Also, the molecular weight is preferably at least about 15 kDa (calculated molecular weight), more preferably at least about 16, 17, 18, 19 or 20 kDa, or more.

Natural gelatines are known to comprise RGD sequences. It is important however that a gelatine molecule does not contain too large parts without RGD motifs. Too large parts of gelatines without RGD sequence reduce the possibility of cell attachment when such a gelatine is used for instance as a coating on a microcarrier. Apparently not all RGD sequences in a gelatine are under all circumstances available for cell attachment. It was found that cell attachment was remarkably improved in gelatines according to the invention compared to gelatines having a stretch of 60 amino acids between RGD morifs.

In a preferred embodiment the RGD-enriched gelatine is prepared by recombinant DNA technology. Recombinant gelatines of this invention are preferably derived, or selected (e.g. "copied"), from natural collageneous sequences, preferably with further modification to fulfill the amino acid sequence criteria described elsewhere herein. Nucleic acid sequences encoding collagens have been generally described in the art. (See, e.g., Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516.).

Gelatin-like Polypeptide Multimers According to the Invention

In a further embodiment multimers of the above monomers are provided. Such multimers thus comprise or consist of at least 2, 3, 4, 5, 6, 7, 8, 9 or 10 repeats of the monomer sequence. Thus, in a further embodiment a recombinant gelatin polypeptide is provided comprising or consisting of a multimer of a monomer sequence described above. Preferably, the monomer repeats are repeats of the same monomer unit (having identical amino acid sequences), although optionally also combinations of different monomer units (having different amino acid sequences, each falling under the criteria above) may be used.

Preferably the monomer units are not separated by spacing amino acids, although short linking amino acids, such as 1, 2, 3, 4 or 5 amino acids, may also be inserted between one or more of the monomers.

In one embodiment the multimers comprise or consist of at least 2, 3, 4, 5, 6, 7, 8, 9 or 10 repeats of SEQ ID NO: 1, and/or a sequence substantially identical to SEQ ID NO: 1. In one embodiment the multimer comprises or consists of SEQ ID NOS: 2, 3, 4, 5, 6, 7, 8, 9 or 10 ($CBE_{2-10}$, respectively).

The (calculated) molecular weight of the multimers may thus range from about 30 kDa to about 200 kDa.

Multimers can be generated using known standard molecular biology methods. An example can be found in Werten et al. in Protein Engineering vol 14, pp 447-454, 2001. When using this method, the multimer protein can be preceded and followed by a few extra amino acids, owing to the use of restriction enzymes sites for the construction of the multimer.

Material and Compositions Comprising the RGD-enriched Monomers and/or Multimers

It was found that recombinant gelatines according to the invention are very suitable for coating cell culture supports which can be used in biotechnological processes or in medical applications. RGD sequences in gelatines can adhere to specific receptors on the cell wall called integrins. These integrins differ in their specificity in recognising cell binding amino acid sequences.

Recombinantly produced gelatine does not suffer from the disadvantage of contamination with pathogens originating from the animal from which the gelatine was derived.

When used as or in combination with a cell culture support, the gelatine-like polypeptides according to the invention functions as a cell binding polypeptide. It has the advantage over other polypeptides that it can also be metabolised by the cells growing on it. A further advantage is that it can be easily digested enzymatically so that cells can be harvested with almost 100% yield.

A further advantage of recombinantly produced gelatines is that the molecular weight (MW) can be kept uniform. Natural gelatines unavoidably have a broad molecular weight distribution with peptides smaller than 5,000 kD up to large polymers with a molecular weight larger than 400,000 kD, resulting from the production method. In particular in combination with microcarrier core beads as cell culture support, a disadvantage of smaller peptides is that they will adhere inside finer pores of the microcarrier which cannot be reached by the cells so that part of the added gelatine is not used. With recombinant production methods the gelatine can be designed with the desired molecular weight, preventing this undesired loss of material.

A cell support comprising a recombinant gelatine according to the invention is provided. Such a cell support may be selected from the group consisting of 1) a cell-culture support, such as a core bead (e.g. a microcarrier bead) or a Petri dish or the like, coated with one or more gelatine-like polypeptides according to the invention;
2) an implant or transplant device (such as hip-, dental-, or other implants, stents, etc.) coated with one or more of the recombinant gelatins according to the invention,
3) a scaffold or matrix for tissue engineering, such as artificial skin matrix material, coated with one or more recombinant gelatine like polypeptides;
4) a wound healing product coated with one or more recombinant gelatine like polypeptides;
5) a tissue adhesive comprising or consisting of one or more recombinant gelatine like polypeptides;
6) a dermal filler.

The recombinant gelatine like proteins offers advantages in that the cell supports, such as microcarriers coated with the polypeptides, have advantageous properties. A key problem in the process of coating microcarrier core beads is the clumping together of beads. In particular such clumping reduces the available surface area for cell attachment and disturbs the size distribution of the microcarriers rendering them unusable. It was found that the use of the polypeptides according to the invention resulted in a more homogenous distribution of coated particle sizes. Also cell adhesion properties of the supports was improved, possibly due to the enhanced protein stability found.

In one embodiment the cell supports provided herein comprise only one recombinant gelatine according to the invention, i.e. selected from one of the polypeptides provided. The product is thus uniform in amino acid sequence, molecular weight, etc. Optionally the peptides may be cross-linked by e.g. chemical cross-linking.

In a different embodiment mixtures of polypeptides according to the invention may be used, such as 2, 3, 4, 5, or more different amino acid sequences according to the invention. The ratios of mixtures may vary, such as 1:1, or 10:1, 50:1, 100:1, 1:100, 1:50, 1:10, and ratios in between these. Optionally also these mixtures may be crosslinked by e.g. chemical cross linking.

When using the recombinant gelatine monomer(s) and/or multimers for coating porous microcarrier beads, preferably polypeptides with a molecular weight of at least about 30 kDa are used, e.g. at least about 30 kDa, 40 kDa, 50 kDa, 60 kDa or 70 kDa or more. The reason for this is that smaller polypeptides enter the pores, thereby not contributing to the cell attachment properties of the coated beads and the coating process may be inefficient, especially if low concentrations of polypeptides are used in the process.

By selecting a molecular weight, within the above specified range, in a coating process the viscosity of the gelatine or gelatine-like protein coating solution can be accurately controlled. Complete or, more important, partial gelling of such a gelatine solution can be prevented while being able to select a high as possible concentration of the gelatine. The uniform gelatine ensures a process of identically coated microcarriers. The uniform coating process allows the use of a minimum amount of gelatine and the use of a minimum volume of gelatine coating solution. All this results in a far more efficient coating process than that is known in the art.

In one embodiment of the invention non-porous core beads are coated with gelatine of the invention. Suitably non-porous core beads are made of polystyrene or glass. Other suitable non-porous materials are known to those skilled in the art.

A particular advantageous embodiment is the process of the invention wherein porous core beads, such as beads from modified dextran or cross-linked cellulose, or (porous) polystyrene, in particular DEAE-dextran, are coated with gelatine of the invention. Other suitable porous materials are known to those skilled in the art, and include e.g. other chemically modified or non-modified polysaccharides.

The size of the beads may vary from 50 μm to 500 μm. Typical mean microcarrier bead sizes are about 100, about 150 or about 200 μm in physiological saline. Size ranges with at least 90% of the beads lying within the range may vary from 80-120 μm, 100-150 μm, 125-175 μm or 150-200 μm.

A wide range of cells may be cultured on microcarriers. For instance, cells from invertebrates, from fish, birds and cells of mammalian origin may be cultivated on microcarriers. Transformed and normal cell lines, fibroblastic and epithelial cells and even genetically engineered cells may be cultivated on microcarriers for various biological applications such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation as well. Cells growing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic studies or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labelled compounds.

Microcarriers may also be used for the depletion of macrophages from a population of spleen cells. DEAE-dextran microcarriers can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers.

As a result of the large surface area to volume ratio provided by microcarriers, they can successfully be used for a variety of biological productions on a laboratory scale as well as an industrial scale of for instance even 4000 liters or more.

Large scale production of expressed products can be accomplished with gelatine-coated microcarriers. Loading of microcarriers in production scale bioreactors is generally 20 g/l, but may be increased up to 40 g/l. Microcarriers may be used in batch and perfusion systems, in stirred cultures, and wave bioreactors, as well as to increase the surface area of traditional stationary monolayers and roller cultures.

In a further preferred embodiment the gelatine or gelatine-like protein is in essence free of hydroxyproline residues. Hydroxylation is a requirement for the formation of triple helices in collagen and plays a role in gelation of gelatine. In particular less than 10%, more preferably less than 5% of the amino acid residues of the recombinant gelatines are hydroxyprolines, preferably the recombinant gelatine is free from hydroxyprolines in applications where the gelling capability of the recombinant gelatine is unfavourable. The hydroxyproline-free recombinant gelatines can be used in higher concentrations, and the solutions will be less viscous requiring less vigorous agitation, resulting in less shear forces on the cultured cells. As described in WO 02/070000 A1, recombinant gelatines which are is essence free from hydroxyprolines do not show immune reactions involving IgE in contrast to natural gelatine.

A process for the preparation of collagen coated microcarriers is described in U.S. Pat. No. 4,994,388. In short providing a core bead with a collagen coating is performed in two steps: coating and fixing. The core beads are suspended in an acidic, aqueous collagen solution (0.01-0.1N acetic acid), and the solution is evaporated to dryness. The dry, collagen-coated beads are then suspended in a solution which contains a protein cross-linking agent such as glutaraldehyde, thus cross-linking the collagen coating. Alternatively, the core beads wetted with the collagen solution are not dried entirely before the start of the fixing step. Variations in coating conditions and alternative coating processes are well within the competence of those skilled in the art.

Recombinant structures can also be designed to incorporate additional positively charged groups, as in U.S. Pat. No. 5,512,474, by building in additional arginines, lysines or histidines. Recombinant production of gelatines allows easy manipulation of the number of positively charged amino acids, meaning positively charged at the pH of the cell culture, in the produced protein. In particular arginine, lysine and histidine carry positive charges. It is well within the reach of the skilled person to design a gelatine with a net positive charge at the pH of the particular cell culture of interest. Cells are normally cultured at a pH of 7-7.5. Thus in a further embodiment of the invention a gelatine or gelatine-like protein is used that has a net positive charge at pH 7-7.5. Preferably the net positive charge is +2, +3, +4, +5, +10 or higher. Thus in a further embodiment the invention relates to a gelatine that has a net positive charge at pH 7-7.5. Preferably the net positive charge is +2, +3, +4, +5, +10 or higher In a further embodiment the invention relates to the use of RGD-enriched gelatines according to the invention to block surface receptors on cells and to make compositions for blocking such receptors. Blocking of receptors of cells is applied in for example inhibiting angiogenesis or in blocking integrins on cardiac fibroblasts.

Cell supports coated with recombinant gelatine according to the invention, on which cells have been grown can be applied during, for example, transplantation of skin or wound treatment or to enhance bone or cartilage (re)growth. It is also possible to coat implant materials with recombinant gelatine of the invention to adhere cells which promote implantation.

In yet another embodiment of the invention a controlled release composition comprising one or more recombinant gelatins according to the invention is provided. The composition may, thus further comprise one or more drugs. The controlled release composition can be administered by injection (subcutaneous, intravenous or intramuscular) or orally or via inhalation. However, the used controlled release composition can also be implanted via surgery. Yet another suitable route of administering is via an external wound dressing or even transdermally.

The controlled release composition preferably comprises the recombinant gelatine in a cross-linked form, e.g. chemically crosslinked. The invention further provides use of a controlled release composition as described herein for the preparation of a medicament for the treatment of pain, cancer therapy, cardiovascular diseases, myocardial repair, angiogenesis, bone repair and regeneration, wound treatment, neural stimulation/therapy or diabetics In a further embodiment the invention relates to RGD-enriched gelatines which are not glycosylated. Glycosylation takes place at the amino acids Asn (N-glycosydic structures), or Ser or Thr (O-glycosydic structures). Glycosylation should be preferably prevented for applications where no immune response is desired. The absence of Asn, Ser and Thr amino acids in the primary sequence is an effective way to prevent the glycosylation in biotechnological production systems using for instance yeast cell cultures.

Furthermore, characteristic for gelatine is the unusual high content of proline residues. Even more characteristic is that in natural gelatine a number of the proline residues is hydroxylated. Most prominent site of hydroxylation is the 4-position resulting in the presence in the gelatine molecule of the unusual amino acid 4-hydroxyproline. In a triplet 4-hydroxyproline is always found in the Y position. The presence of the hydroxyproline residues is responsible for the fact that a gelatine molecule in its secondary structure can adopt a helical conformation. Thus, it is preferred that the gelatines to be used according to the invention in applications in which the gelling property is unfavourable contain less than 5%, preferably less than 3%, most preferably less than 1% of hydroxyproline residues.

The RGD-enriched gelatines according to the invention can be produced by recombinant methods as disclosed in EP-A-0926543, EP-A-1014176 or WO01/34646. Also for enablement of the production and purification of gelatines of the invention reference is made to the examples in EP-A-0926543 and EP-A-1014176.

Starting from a natural nucleic acid sequence encoding (part of) a collagen, also point mutations can be applied so as to yield a sequence encoding an RGD enriched gelatine according to the invention. Based on the known codons a point mutation can be performed so that an RGX sequence after mutation will yield an RGD sequence, alternatively also an YGD sequence can be mutated to yield an RGD sequence. Also it is possible to carry out two mutations so that an YGX sequence will give an RGD sequence. Also it may be possible to insert one or more nucleotides or delete one or more nucleotides giving rise to a desired RGD sequence.

Thus the gelatine-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* or *Hansenula* offers an example of a very suitable expression system. Use of *Pichia pastoris* as an expression system is disclosed in EP-A-0926543 and EP-A-1014176. In one embodiment the microorganism is free of active post-translational processing mechanism such as in particular hydroxylation of proline and also hydroxylation of lysine. In another embodiment the host system has an endogenic proline hydroxylation activity by which the recombinant gelatine is hydroxylated in a highly effective way. The selection of a suitable host cell from known industrial enzyme producing fungal host cells specifically yeast cells on the basis of the required parameters described herein rendering the host cell suitable for expression of recombinant gelatine-like proteins suitable in compositions according to the invention in combination with knowledge regarding the host cells and the sequence to be expressed will be possible by a person skilled in the art.

Thus in one aspect the invention also concerns a method for producing a recombinant gelatine according to the present invention, said method comprising
  preparing an expression vector comprising a nucleic acid sequence encoding a polypeptide according to claims 1-4 operably linked to a suitable promoter,
  expressing said nucleic acid sequence in a methylotrophic yeast,
  culturing said yeast under suitable fermentation conditions to allow expression of said nucleic acid sequence;
  optionally purifying said polypeptide from the culture
Sequences
SEQ ID NO 1: CBE monomer ($CBE_1$)
SEQ ID NO 2: $CBE_2$
SEQ ID NO 3: $CBE_3$
SEQ ID NO 4: $CBE_4$
SEQ ID NO 5: $CBE_5$
SEQ ID NO 6: $CBE_6$
SEQ ID NO 7: $CBE_7$
SEQ ID NO 8: $CBE_8$
SEQ ID NO 9: $CBE_9$
SEQ ID NO 10: $CBE_{10}$
SEQ ID NO 11: CBE In one embodiment a gelatin according to the present invention comprises or consists of of SEQ ID NO: 2, 3, 4, 5, 6, 7, 8, 9 or 10. In one embodiment the multimer recombinant gelatins according to the present invention, e.g. SEQ ID NO 2-10 are extended with a glycine (G) at the carboxy-terminus. Thus recombinant gelatins according to the present invention include (SEQ ID NO 1)$_x$G, wherein x is an integer selected form 2-10. In one embodiment the multimer recombinant gelatins according to the present invention, e.g. SEQ ID NO 2-10 are preceded by a glycine-alanine-proline triplet (GAP) at the amino-terminus. Thus recombinant gelatins according to the present invention include GAP(SEQ ID NO 1)$_x$, wherein x is an integer selected form 2-10. In one embodiment the multimer recombinant gelatins according to the present invention, e.g. SEQ ID NO 2-10 are preceded by a glycine-alanine-proline triplet (GAP) at the amino-terminus and extended with a glycine (G) at the carboxy-terminus. Thus recombinant gelatins according to the present invention include GAP(SEQ ID NO 1)$_x$G.

EXAMPLES

Example 1

An RGD-enriched gelatine was produced based on a nucleic acid sequence that encodes for a part of the gelatine amino acid sequence of human COL1A1-1 and modifying this nucleic acid sequence. The methods as disclosed in EP-A-0926543, EP-A-1014176 and WO01/34646 were used. This RGD-enriched gelatine is named CBE and the sequence of this RGD-enriched gelatine according to the invention is given in SEQ ID NO: 11.
Amino Acid Sequence of CBE (SEQ ID NO: 11):
  GAPGAPGLQGAPGLQGMPGERGAAGLPG-
PKGERGDAGPKGADGAPGAPGLQGMPGERGAAG
LPGPKGERGDAGPKGADGAPGKDGVR-
GLAGPIGPPGERGAAGLPGPKGERGDAGPKGADGAP
GKDGVRGLAGPIGPPGPAGAPGAPGLQG-
MPGERGAAGLPGPKGERGDAGPKGADGAPGKDGV
RGLAGPI
192 amino acids in length; comprising 4 RGD motifs
  From the sequence of CBE, the sequence of CBE monomer (SEQ ID NO: 1) has been derived.
Amino Acid Sequence of CBE Monomer (SEQ ID NO: 1):
  GAPGLQGAPGLQGMPGERGAAGLPGP-
KGERGDAGPKGADGAPGAPGLQGMPGERGAAGLPG
PKGERGDAGPKGADGAPGKDGVRGLAG-
PIGPPGERGAAGLPGPKGERGDAGPKGADGAPGKD
GVRGLAGPIGPPGPAGAPGAPGLQG-
MPGERGAAGLPGPKGERGDAGPKGAD-
GAPGKDGVRGL AGPP
189 amino acids in length; comprising 4 RGD motifs
  Via standard subcloning methods multimers comprising the CBE monomer have been prepared, e.g. SEQ ID NO: 2 to SEQ ID NO: 10.
Amino Acid Sequence CBE Trimer used in the Examples Below which is Based on $CBE_3$ (SEQ ID NO: 3), Preceded by GAP and Extended with a Glycine (G):

GAP(GAPGLQGAPGLQGMPGERGAAGLPGP-
KGERGDAGPKGADGAPGAPGLQGMPGERGAAG
LPGPKGERGDAGPKGADGAPGKDGVR-
GLAGPIGPPGERGAAGLPGPKGERGDAGPKGADGAP
GKDGVRGLAGPIGPPGPAGAPGAPGLQG-
MPGERGAAGLPGPKGERGDAGPKGADGAPGKDGV
RGLAGPX)$_3$G 571 amino acids in length; comprising 12 RGD motifs Amino Acid Sequence CBE Pentamer used in the Examples Below which is Based on CBE$_5$ (SEQ ID NO: 5) Preceded by GAP and Extended with a Glycine (G):

GAP(GAPGLQGAPGLQGMPGERGAAGLPGP-
KGERGDAGPKGADGAPGAPGLQGMPGERGAAG
LPGPKGERGDAGPKGADGAPGKDGVR-
GLAGPIGPPGERGAAGLPGPKGERGDAGPKGADGAP
GKDGVRGLAGPIGPPGPAGAPGAPGLQG-
MPGERGAAGLPGPKGERGDAGPKGADGAPGKDGV
RGLAGPP)$_5$G 949 amino acids in length; comprising 20 RGD motifs Example 2

Preparation of Microcarriers Beads

Polystyrene beads with an average diameter of 100 micrometers arc used. The heterobifunctional cross-linking agent, BBA-EAC-NOS, is used to covalently immobilise gelatin onto polystyrene beads. The BBA-EAC-NOS is added to the polystyrene beads and allowed to adsorb. Next, gelatin is added and is allowed to react with the NOS synthetic polymer to produce covalent coupling to the spacer. Then the beads are photoactivated (at 320 nm) to covalently immobilise the spacer (and covalently coupled gelatin) to the polystyrene beads. Finally, loosely adherent gelatine is removed by overnight washing with the mild detergent Tween 20 in phosphate buffered saline (pH 7.2).

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm² flasks at 37 DEG C. in a 5% $CO_2$ environment. Vero and NRK-49F cells were cultured in Dulbecco's Modified Eagles's Medium (DMEM), CHO cells were cultured in Ham's F-12 Nutrient Mixture, and MDCK cells were cultured in Minimum Essential Medium (MEM) with Earle's salts.

With the Vero and CHO cells, the medium was supplemented with 10% fetal bovine serum (FBS), 2 mM L-glutamine, 20 mM HEPES buffer, 1 mM sodium pyruvate, 100 ug/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 µg/ml streptomycin, 100 units/ml penicillin, and 0.25 µg/ml of amphotericin B (final pH 7.1). With the MDCK cells, the MEM was supplemented with 10% FBS, 2 mM L-glutamine, non-essential amino acids (0.1 mM each), and 100 µg/ml streptomycin, 100 units/ml penicillin, and 0.25 µg/ml of amphotericin B (final pH 7.1).

In order to standardise the physiology of cells prior to each experiment, cells were passed into 150 cm² flasks 2 to 3 days prior to inoculation of microcarrier beads. Cells were trypsinised (0.05% trypsin, 0.53 mM EDTA in PBS) for removal from the flasks. For the microcarrier experiments, the cells were centrifuged to remove the trypsin medium and resuspended to about 1.times.10⁶ cells/ml in culture medium. The viable cell concentration was determined by Trypan dye exclusion (0.4% Trypan blue in 0.9% saline).

Cell Culture and Assays in Spinner Flasks

For the cell attachment assay, 20 mg/ml of coated polystyrene beads were used and the cell concentration was 1.5.times.10⁵ cells/ml for each cell type.

Microcarriers were cultured with 100 ml cultures being maintained in 250 ml spinner vessels and stirred with suspended magnetic impellers (50 rpm).

The kinetics of cell attachment were assayed as a decrease in supernatant cell concentration. For sample removal the agitation was stopped briefly (about 30 seconds) at which time the microcarriers settled and a supernatant sample was removed for cell quantitation as described below.

For the cell counts, the cells were stained by mixing with an equal volume of crystal violet (0.1% w/w) in 0.1 M citric acid, and then counted with a hemocytometer. Cell depletion from the medium was used as an indicator of cells attached to beads.

To verify that cells removed from the medium were indeed attached to microcarriers (and not lysed), cells attached to microcarriers were quantitated at the end of each cell attachment assay. One ml aliquots of well-agitated carrier medium were removed, the microcarriers were allowed to settle, and the settled microcarriers were resuspended in crystal violet/citric acid as described above. After incubating 1 hour at 37 DEG C., the suspension was sheared by sucking into and out of a Pasteur pipette to release nuclei, which were quantitated with a haemocytometer.

Gelatin CBE (SEQ ID NO: 11) was used as a microcarrier coating according to the foregoing procedure and compared with a reference RGD-enriched gelatin with sequence identifier number 2 having four RGD sequences as disclosed in US 2006/0241032. CBE gave improved results in terms of numbers of cell depletion from the starting culture medium and also in terms of cell attachment to microcarriers. This improvement may be due to improved stability of the CBE gelatine compared to the sequence with identifier number 2 as disclosed in US 2006/0241032.

Also CBE trimer and CBE pentamer are used as a microcarrier coating according to the foregoing procedure and compared with a trimer, a tetramer and a quintamer of RGD-enriched gelatin with sequence identifier number 2 as disclosed in US 2006/0241032. Probably due to their improved stability, CBE trimer and CBE pentamer show improved cell attachment to microcarriers compared to the multimeric gelatins based on the sequence with identifier number 2 as disclosed in US 2006/0241032. Also particle size measurements of CBE trimer and CBE pentamer coated microcarriers after keeping the coated microcarriers for 24 hours and immediately after the cell attachment assay show a more homogeneous distribution of particle sizes compared to the multimeric gelatins based on the sequence with identifier number 2 as disclosed in US 2006/0241032.

The invention claimed is:

1. A recombinant gelatin comprising or consisting of a polypeptide with an amino acid sequence of at least 90% sequence identity to SEQ ID NO: 1.

2. The recombinant gelatin comprising a multimer of a sequence according to claim 1.

3. The recombinant gelatin according to claim 2, wherein the multimer comprises at least 3, 4 or 5 sequences, each of at least 90% sequence identity to SEQ ID NO: 1.

4. The recombinant gelatin according to claim 1, wherein the gelatin comprises SEQ ID NO: 2, 3, 4, 5, 6, 7, 8, 9 or 10.

5. The recombinant gelatin according to claim 2, wherein the gelatin comprises SEQ ID NO: 2, 3, 4, 5, 6, 7, 8, 9 or 10.

6. The recombinant gelatin according to claim 3, wherein the gelatin comprises SEQ ID NO: 3, 4, 5, 6, 7, 8, 9 or 10.

7. A recombinant gelatin according to claim 1 which comprises at least 3, 4 or 5 sequences, each with at least 90% sequence identity to SEQ ID NO: 1, wherein the gelatin comprises SEQ ID NO: 3, 4, 5, 6, 7, 8, 9 or 10.

8. A cell support comprising a recombinant gelatin according to claim 1.

9. A cell support comprising a recombinant gelatin according to claim 7.

10. The cell support according to claim 8, said cell support being selected from the group consisting of a recombinant gelatin coated implant or transplant material, a recombinant gelatin coated scaffold for tissue engineering, a dental product, a wound healing product, artificial skin matrix material and a tissue adhesive.

11. A controlled release composition comprising a recombinant gelatin according to claim 1.

12. A controlled release composition comprising a recombinant gelatin according to claim 7.

13. The controlled release composition according to claim 11, wherein the recombinant gelatin is crosslinked.

14. The controlled release composition according to claim 12, wherein the recombinant gelatin is crosslinked.

15. A method for prevention of platelet aggregation or to prevent tissue adhesion after surgery of a patient comprising administering to the patient the cell support as described in claim 8.

16. A method for prevention of platelet aggregation or to prevent tissue adhesion after surgery of a patient comprising administering to the patient the cell support as described in claim 9.

17. A method for producing a recombinant gelatin, said method comprising:

a) preparing an expression vector comprising a nucleic acid sequence encoding a polypeptide according to claim 1 operably linked to a suitable promoter;

b) expressing said nucleic acid sequence in a methylotrophic yeast;

c) culturing said yeast under suitable fermentation conditions to allow expression of said nucleic acid sequence; and optionally purifying said polypeptide from the culture.

18. A recombinant gelatin according to claim 1 comprising a polypeptide with an amino acid sequence of at least 90% sequence identity to SEQ ID NO: 1 wherein sequence identity is an alignment having no more than 3 gaps.

19. The recombinant gelatin according to claim 1, wherein the gelatin consists of SEQ ID NO: 2, 3, 4, 5, 6, 7, 8, 9 or 10.

20. The recombinant gelatin according to claim 2, wherein the gelatin consists of SEQ ID NO: 2, 3, 4, 5, 6, 7, 8, 9 or 10.

21. The recombinant gelatin according to claim 3, wherein the gelatin consists of SEQ ID NO: 3, 4, 5, 6, 7, 8, 9 or 10.

22. The recombinant gelatin according to claim 1, wherein the polypeptide consists of an amino acid sequence with at least 90% sequence identity to SEQ ID NO: 1.

* * * * *